United States Patent [19]

Stoddart et al.

[11] Patent Number: 4,696,918

[45] Date of Patent: Sep. 29, 1987

[54] SOLUBILIZED PLATINUM COMPOUND

[75] Inventors: James F. Stoddart, Sheffield; David R. Alston, Tonbridge, both of England

[73] Assignee: Johnson Matthey Public Limited Company, London, England

[21] Appl. No.: 793,341

[22] Filed: Oct. 31, 1985

[30] Foreign Application Priority Data

Nov. 2, 1984 [GB] United Kingdom ............... 8427767
Nov. 16, 1984 [GB] United Kingdom ............... 8429030
Feb. 11, 1985 [GB] United Kingdom ............... 8503432

[51] Int. Cl.$^4$ .................. C08G 59/00; C08G 65/08; C07F 15/00
[52] U.S. Cl. ..................... 514/58; 536/103; 536/121; 556/137
[58] Field of Search ............... 536/103, 121; 514/58; 556/137

[56] References Cited

U.S. PATENT DOCUMENTS

| | | | |
|---|---|---|---|
| 2,959,580 | 11/1960 | Schlenk et al. | 536/103 X |
| 3,252,863 | 5/1964 | Lindvall et al. | 536/103 X |
| 3,821,192 | 6/1974 | Montgomery et al. | 536/103 |
| 4,180,567 | 12/1979 | Herb | 514/58 X |
| 4,234,499 | 11/1980 | Hoeschele et al. | 536/117 X |
| 4,500,465 | 2/1985 | Amundsen | 536/137 |
| 4,518,588 | 5/1985 | Szejtli et al. | 536/103 X |
| 4,551,524 | 11/1985 | Kidani et al. | 536/121 |
| 4,565,884 | 1/1986 | Andrulis et al. | 536/121 X |
| 4,575,550 | 3/1986 | Totani | 536/121 |
| 4,584,392 | 4/1986 | Smith et al. | 536/121 X |
| 4,587,331 | 5/1986 | Hlavka et al. | 536/121 X |

OTHER PUBLICATIONS

Chemical Abstracts 98 34900g (1983).
Chemical Abstracts 86 64751d (1977).
Chemical Abstracts 104 194260u (1985).
Chemical Abstracts 104 178027t (1985).

*Primary Examiner*—Helen M. S. Sneed
*Attorney, Agent, or Firm*—Cushman, Darby & Cushman

[57] ABSTRACT

The anti-cancer compound 1,1-cyclobutanedicarboxylatediammineplatinum(II) is rendered more water-soluble by formation of its inclusion compound with α-cyclodextrin.

7 Claims, 5 Drawing Figures

SOLUBILIZED PLATINUM COMPOUND

This invention relates to platinum compounds for use in cancer chemotherapy, and in particular provides a platinum co-ordination compound which is solubilised to render it more easily administrable and/or assimilable into the systemic circulation.

Since the initial discovery by Rosenberg that the compound known generically as "cisplatin" is an active anti-cancer drug, there have been many attempts by various groups of workers to provide analogous compounds which are either more active and/or less toxic, and/or more soluble in aqueous media. Enhanced solubility renders the compound able to form a more concentrated solution for either parenteral or oral administration which may result in a higher blood concentration or which may provide a convenient way of increasing the dosage level. This is particularly the case where the patient has a high level of platinum excretion and/or where the drug is relatively non-toxic. Increased solubility would also render the compound more easy to handle, both in distribution and storage and also in the clinic. Where it is desired to increase solubility in aqueous media, it has in the past been proposed to incorporate in the molecule one or more known solubilising groups such as carboxylic acid or sulphonic acid, or to prepare the compound as an anion of one of these acids together with a water-soluble, preferably alkali metal, cation. Such proposals have however met with little success, the activity of a given compound being apparently related to some inherent chemical property or moiety rather than purely to its solubility. Even attempts to improve the solubility of compounds which inherently have higher activity than cisplatin have met with little success.

One compound which is currently showing promise as a second-generation drug is the compound 1,1-cyclobutanedicarboxylatediammineplatinum(II), disclosed per se in GB 1380228. The solubility of this compound is quoted in the literature as being 18.5 mg/ml (50 mmolar) (Cleare et al, Biochemie, 1978, vol. 60, pages 835-850). This compound is relatively non-toxic when compared with certain other platinum-containing compounds, particularly cisplatin where the dose-limiting factor is kidney toxicity. This effect is reduced dramatically, and other side effects such as myelosuppression and nausea are mitigated, by the use of 1,1-cyclobutanedicarboxylatediammineplatinum(II).

It is known that the aqueous solubility of certain pharmacologically-active compounds may be increased by formation of their inclusion compounds with α, β and/or γ cyclodextrin. Hitherto, however, attempts to form inclusion compounds of platinum coordination compounds with cyclodextrins have not been successful. Consequently it was generally believed that such inclusion compounds could not be prepared. We have now found, however, that the cyclobutane moiety of the compound 1,1-cyclobutanedicarboxylatediammineplatinum(II) may be incorporated into the ring structure of a particular cyclodextrin, namely α-cyclodextrin, to form an inclusion compound and that the said inclusion compound has an aqueous solubility some four-fold greater than the parent compound.

Accordingly, therefore, the present invention provides the inclusion compound of 1,1-cyclobutanedicarboxylatediammineplatinum(II) and α-cyclodextrin.

The invention also provides a pharmaceutical composition comprising the inclusion compound of 1,1-cyclobutanedicarboxylatediammineplatinum(II) and α-cyclodextrin in admixture or solution with an inert pharmaceutically-acceptable diluent, carrier or solvent, optionally in unit dosage form.

Preperably the solvent comprises water. Optionally, compositions according to the invention may also include additives such as stabilising agents.

α-Cyclodextrin is a cyclic oligosaccharide consisting of 6 glucose units and has the following chemical formula:

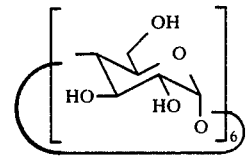

Inclusion compounds according to the invention generally have the platinum compound and the cyclodextrin in a molar ratio of 1:1, since this ratio gives the maximum increase in solubility, although for certain purposes it may be desirable to have an excess of cyclodextrin.

Quantitative evidence for the formation of the preferred compound according to the invention, that is, the 1:1 compound of α-cyclodextrin and 1,1-cyclobutanedicarboxylatediammineplatinum(II) (hereinafter referred to as Pt(NH$_3$)$_2$.CBDCA) is given by the aqueous solubility: approximately 200 mM concentrations can be attained at room temperature when an aqueous solution of α-cyclodextrin (0.6 mol equiv.) is employed to dissolve the platinum complex compared with only 50 mM concentrations in the absence of α-cyclodextrin. Accordingly, the invention also includes in a further aspect an aqueous solution comprising the compound 1,1-cyclobutanedicarboxylatediammineplatinum(II), wherein the said compound is present as a 1:1 inclusion compound with α-cyclodextrin and the concentration is greater than 50 mM, preferably in the range 50-200 mM, at room temperature.

Structure determination of the preferred compound will now be described with reference to the accompanying drawings of which:

We have studied the association constant for the preferred compound according to the invention by a micro-calorimetric method which involves measuring the heat evolved when solutions of the platinum(II) compound and α-cyclodextrin are mixed and also by using a $^1$H n.m.r. spectroscopic approach.

For the microcalorimetry experiments, a solution of the platinum complex (0.02366 mol kg$^{-1}$) in water was mixed with a range of aqueous solutions of α-cyclodextrin (ca. 0.01–0.1 mol kg$^{-1}$) in a batch calorimeter operating at 25° C. A series of preliminary experiments was performed so that corrections for the contributions arising from the enthalpy of dilution of the two solutes could be made. The expression linking the enthalpy change per mol ($\Delta H$) of Pt(NH$_3$)$_2$.CBDCA to the final molalities of both this guest (G) and the α-cyclodextrin host (H) and to the equilibrium constant ($K_a$) and the standard enthalpy change ($\Delta H^\ominus$) for the equilibrium, $$H + G \rightleftharpoons H \cdot G,$$

is $$K_a = \Delta H \cdot \Delta H^\ominus / (\Delta H^\ominus [H] - \Delta H [G])(\Delta H^\ominus - \Delta H) \quad (1)$$

Figure 1:
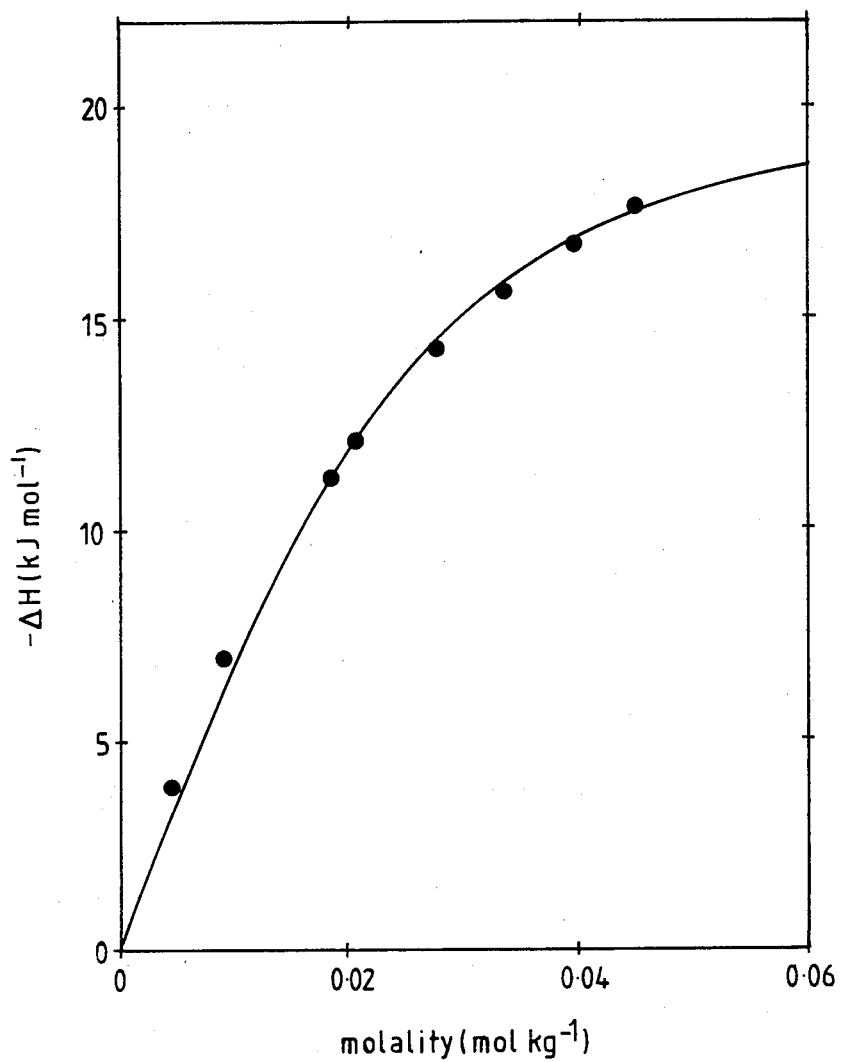
FIG. 1 is a graph of the molar enthalpy of association against molality of the α-cyclodextrin.

Equation (1) was solved using a non-linear least squares routine to give $K_a = 199 \pm 10$ mol$^{-1}$ kg and $\Delta H^\ominus = -21.0 \pm 2.0$ kJ mol$^{-1}$. The results are displayed in FIG. 1, which shows the molar enthalpy of association of Pt(NH$_3$)$_2$.CBDCA with α-cyclodextrin as a function of the molality of the α-cyclodextrin. In the Figure, the filled circles denote experimental points and the line denotes the analysis obtained using Equation (1). It is seen that good correlation is obtained between theory and practice.

Figure 2:
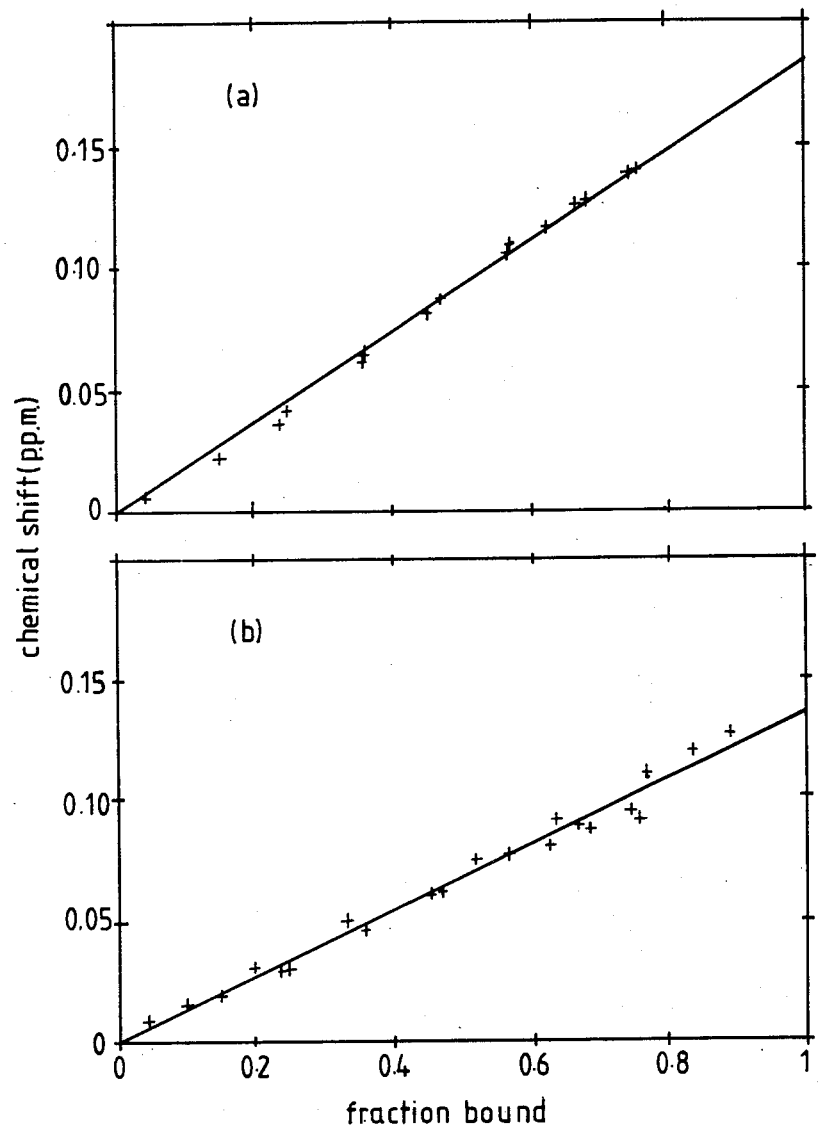
FIG. 2 shows two graphs of corrected chemical shifts of H-3 protons in α-cyclodextrin (a) and H-a protons in Pt(NH$_3$)$_2$.CBDCA (b) as a function of the fraction bound.

For the spectroscopic approach, two types of spectroscopic investigations were performed in D$_2$O at ca. 22° C. using a Bruker AM250FT Spectrometer. In the first series of experiments, equimolar solutions of Pt(NH$_3$)$_2$.CBDCA and α-cyclodextrin were studied at various dilutions and, in the second series of experiments, the concentration of the platinum complex was kept constant and the concentration of the α-cyclodextrin was varied. When processing the chemical shift data, corrections were made to allow for the tendency of α-cyclodextrin to self-associate. FIG. 2 shows the corrected chemical shifts for the H-3 protons in α-cyclodextrin and the H-a protons in Pt(NH$_3$)$_2$.CBDCA as a function of the fraction bound. The latter was calculated from the equilibrium constant, corrected to the aquamolal scale, obtained from the microcalorimetric measurements. It is apparent from examination of FIG. 2 that there is excellent agreement between the n.m.r. and thermodynamic results. The values of the equilibrium constant and the standard enthalpy and entropy ($\Delta S^\ominus = -27$ J K$^{-1}$ mol$^{-1}$) changes recorded in FIG. 2 indicate that Pt(NH$_3$)$_2$.CBDCA has a very marked tendency to associate with α-cyclodextrin in water.

The magnitudes of the chemical shift changes for H-3 and H-5 relative to those for the other glucopyranosidic protons in α-cyclodextrin and large shifts observed for H-a and H-b on the CBDCA ligand of Pt(NH$_3$)$_2$.CBDCA indicate that those pairs of host and guest protons are in propinquity, i.e. it is the CBDCA ligand of the guest which penetrates the host cavity.

We have also prepared crystals of the above preferred compound according to the invention by slow cooling and evaporation of a hot (80° C.) saturated aqueous solution of α-cyclodextrin (105 mg/1 ml) also saturated with the platinum(II) compound (34.7 mg). The resulting crystals (m.pt. 235°–255° C.) were examined by X-ray crystallography which confirmed that the cyclobutane ring of the platinum(II) compound was bound inside the cavity of the α-cyclodextrin, with the possibility of hydrogen bonds from the secondary hydroxyl groups of the α-cyclodextrin to both the carbonyl oxygen atoms and the ammine ligands of the platinum(II) compound.

Crystal data were obtained on a Nicolet R3 m diffractometer with Cu-$K_\alpha$ radiation (graphite monochromator) using ω-scans.

Data was as follows:

C$_{42}$H$_{82}$O$_{39}$N$_2$Pt, $M = 1434.1$, orthorhombic, space group $P2_12_12_1$, $a = 10.102(2)$, $b = 13.526(4)$, $c = 41.971(9)$ Å, $U = 5735$ Å, $Z = 4$, $\mu$(Cu-$K$) = 55 cm$^{-1}$, $D_c = 1.67$ g cm$^{-3}$.

The structure was solved by the heavy atom method and refined anisotropically using absorption corrected data to $R = 0.041$, $R_w = 0.044$ currently for 4211 independent reflections [$\theta \leq 58°$, $|F_o| > 3\sigma(|F_o|)$].

Figure 3:
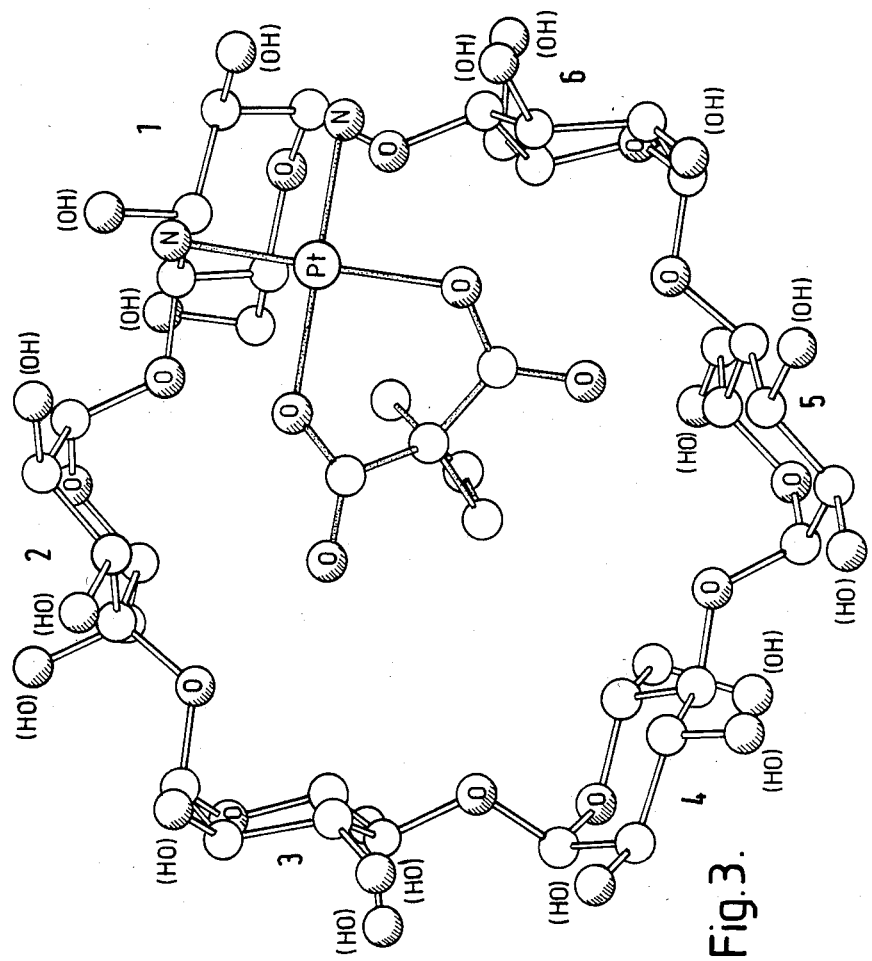
FIG. 3 is a plan view of the crystal structure of the compound as a framework representation.
Figure 4:
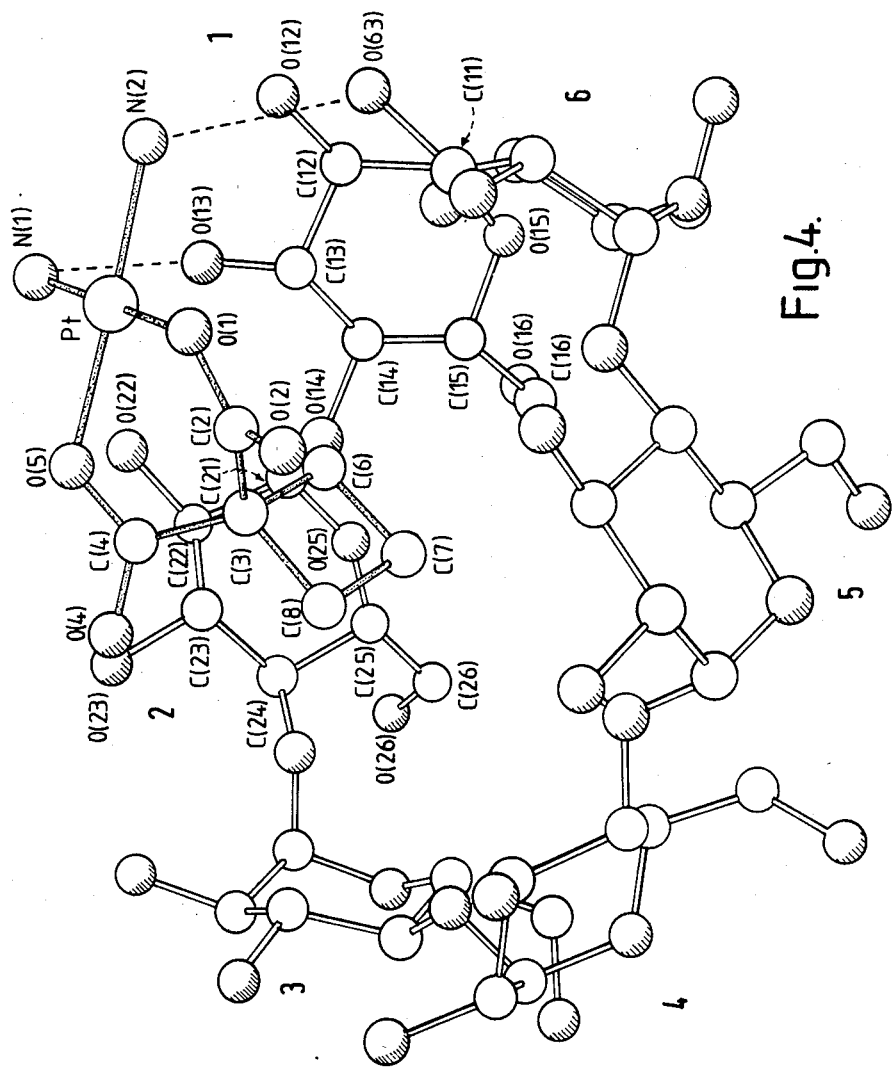
FIG. 4 is a side view of the structure shown in FIG. 4.
Figure 5:
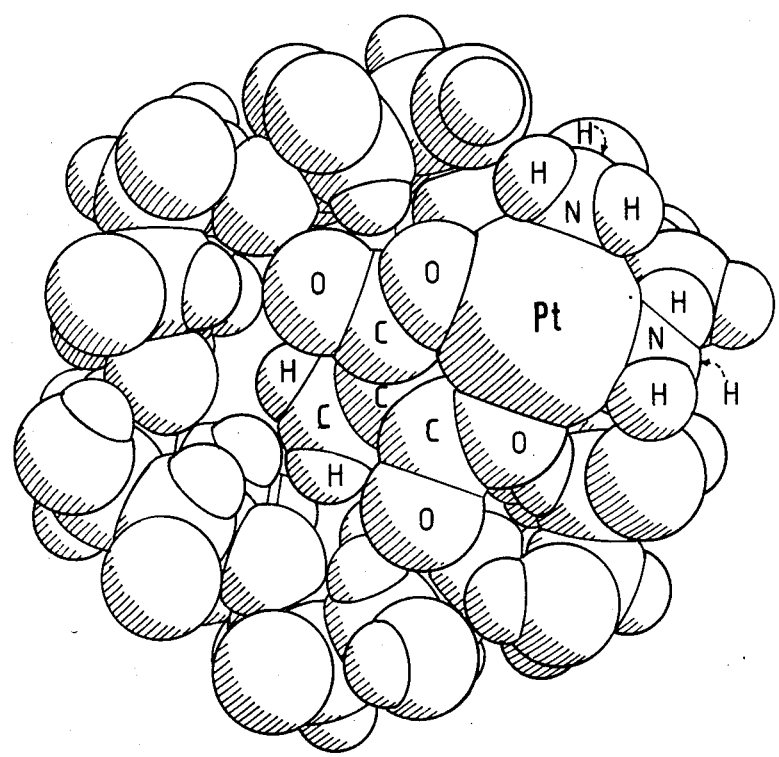
FIG. 5 is a space-filling representation of the structure shown in FIGS. 3 and 4.

The crystal structure is illustrated in FIGS. 3, 4 and 5. FIGS. 3 and 4 show plan and side views respectively of framework representations of the 1:1 adduct. The space-filling representation in FIG. 5 illustrates the degree of penetration of the cyclobutane ring of Pt(NH$_3$)$_2$CBDCA into α-cyclodextrin. The cyclodextrin has a characteristic open slightly bucket-shaped conformation with local pseudo $C_6$ symmetry. The bound complex is positioned with the cyclobutane ring oriented approximately over the centre of the α-cyclodextrin torus, its plane lying parallel to the '6-fold' axis of the host. The cyclobutane ring is inserted into the α-cyclodextrin lying 1.03 and 0.35 Å respectively below the mean plane of the oxygen atoms associated with the twelve secondary hydroxyl groups. Carbon atom C(7) lies 0.94 Å above the mean plane of the six glycosidic oxygen atoms. The ammine ligands are oriented, for the most part, over one of the α-D-glycopyranosidic units which is, in turn, significantly more tilted with respect to the principle axis of the α-cyclodextrin host. There are two [N—H . . . O] hydrogen bonds between the ammine ligands and this cyclodextrin molecule, one between N(1) and O(13) of 3.14 Å and the other between N(2) and O(63) of 2.94 Å. Surprisingly, there appear to be no hydrogen bonds between the CBDCA carbonyl oxygen atoms and the secondary hydroxyl groups of the host cyclodextrin molecule. However, there are hydrogen bonds both from these carbonyl oxygen atoms and from the ammine hydrogen atoms to symmetry-related cyclodextrin molecules. There are also hydrogen bonds between five water molecules and both α-cyclodextrin hydroxyl groups and the Pt(NH$_3$)$_2$CBDCA carbonyl oxygen atoms and ammine hydrogen atoms.

The invention also includes a method for the preparation of the inclusion compound of 1,1-cyclobutanedicarboxylatediammineplatinum(II) and α-cyclodextrin in aqueous solution, the method comprising adding one of the said compounds to an aqueous solution containing the other of said compounds. Optionally, the inclusion compound may be prepared in powder form by lyophilisation of the resulting aqueous solution.

Tests were carried out to determine the pharmacokinetic and toxicity properties of the 1:1 inclusion compound of Pt(NH$_3$)$_2$.CBDCA with α-cyclodextrin compared with Pt(NH$_3$)$_2$.CBDCA alone. In particular, studies were carried out on the distribution of platinum in the blood, urine and faeces following intravenous administration of the compounds, and the in vitro cytotoxicity was measured, as were the in vivo haematotoxicity and nephrotoxicity. For the in vivo studies, test animals in all cases were male Wistar albino rats. It was found in general that the compounds were similar when administered systemically in that both showed a similar biphasic decay of blood platinum, faecal levels were similar at 4–5% Pt excretion in 24 hours and urine levels were similar at 65–67% Pt excretion in 24 hours. In vitro toxicity tests showed that the compounds are of similar toxicity towards CHO and HeLa cells, and there was no significant temporal difference towards HeLa cells at different drug incubation times over the range 0.25–3 hours, the compound concentration being 1.0 mM. In haematotoxicity and nephrotoxicity testing, blood samples taken on days 1, 4, 8, 12 and 16 after injection were analysed for haematocrit, total white blood cell count, differential white blood cell count and plasma urea nitrogen. The kidneys were also subjected to histological examination. Results as between the two test compounds were similar although the compound according to the invention appeared to cause slightly less anaemic and myelosuppressive response. Plasma urea nitrogen levels remained constant throughout the study period, indicating no gross nephtrotoxicity. This was in agreement with measurements of urine protein levels where no obvious proteinuria was observed over a three day period. Some nuclear enlargement of the kidneys was apparent on histological examination.

The results quoted above show that the compound according to the invention is at least equivalent to 1,1-cyclobutanedicarboxylatediammineplatinum(II) in its pharmacokinetics and toxicity, thus rendering the substantially increased solubility of the inclusion compound significant in terms of convenience in handling and clinical utility.

We claim:
1. The inclusion compound of 1,1-cyclobutanedicarboxylatediammineplatinum(II) and α-cyclodextrin.
2. A pharmaceutical composition comprising the inclusion compound of 1,1-cyclobutanedicarboxylatediammineplatinum(II) and α-cyclodextrin in admixture or solution with an inert, pharmaceutically-acceptable diluent, carrier or solvent.
3. A composition according to claim 2 in which the compound is in solution in water.
4. A pharmaceutical composition consisting of an aqueous solution comprising the compound 1,1-cyclobutanedicarboxylatediammineplatinum(II), wherein the said compound is present as a 1:1 inclusion compound with α-cyclodextrin and the concentration is greater than 50 mM at room temperature.
5. A composition according to claim 2 in unit dosage form.
6. A method for the preparation of the inclusion compound of 1,1-cyclobutanedicarboxylatediammineplatinum(II) and α-cyclodextrin in aqueous solution, the method comprising adding one of the said compounds to an aqueous solution containing the other of the said compounds.
7. A method for the preparation of the inclusion compound of 1,1-cyclobutanedicarboxylatediammineplatinum(II) and α-cyclodextrin in powder form, the method comprising lyophilisation of the product of the method of claim 6.

* * * * *